United States Patent [19]

Sivash

[11] 4,384,373

[45] May 24, 1983

[54] DEVICE FOR FUNCTIONAL RESTORATION OF AN EXTREMITY

[76] Inventor: Konstantin M. Sivash, ulitsa B. Pirogovskaya, 37/43-A, kv. 49, Moscow, U.S.S.R.

[21] Appl. No.: 243,789

[22] Filed: Mar. 16, 1981

[51] Int. Cl.³ ............................................... A61F 1/04
[52] U.S. Cl. ..................................... 3/1.91; 128/92 C
[58] Field of Search .................... 3/1.91, 1.911, 1.912, 3/1.913; 128/92 BC, 92 C, 92 CA

[56] References Cited

U.S. PATENT DOCUMENTS 3,662,405   5/1972   Bortz et al. ................... 128/92 C X

FOREIGN PATENT DOCUMENTS 2805868   8/1979   Fed. Rep. of Germany ....... 3/1.912
578063  11/1977   U.S.S.R. ............................ 128/92 C
648221   2/1979   U.S.S.R. ................................. 3/1.91

Primary Examiner—Richard J. Apley
Assistant Examiner—David J. Isabella
Attorney, Agent, or Firm—Steinberg & Raskin

[57] ABSTRACT

The device disclosed in the present invention for functional restoration of an extremity comprises an artificial hip joint, an artificial knee joint and artificial femoral diaphysis. The artificial femoral diaphysis is made up of a cylindrical column having a through longitudinal bore, and a rod, both said column and said rod being interlinked telescopically. The cylindrical column is inseparably linked to the artificial knee joint, while the rod is inseparably linked to the artificial hip joint at one of its ends and with the other end is fitted into the bore of the column, said other rod end carrying a threaded sleeve which engages a motion screw rotatably mounted in the column for the rod to travel with respect to the column.

3 Claims, 4 Drawing Figures

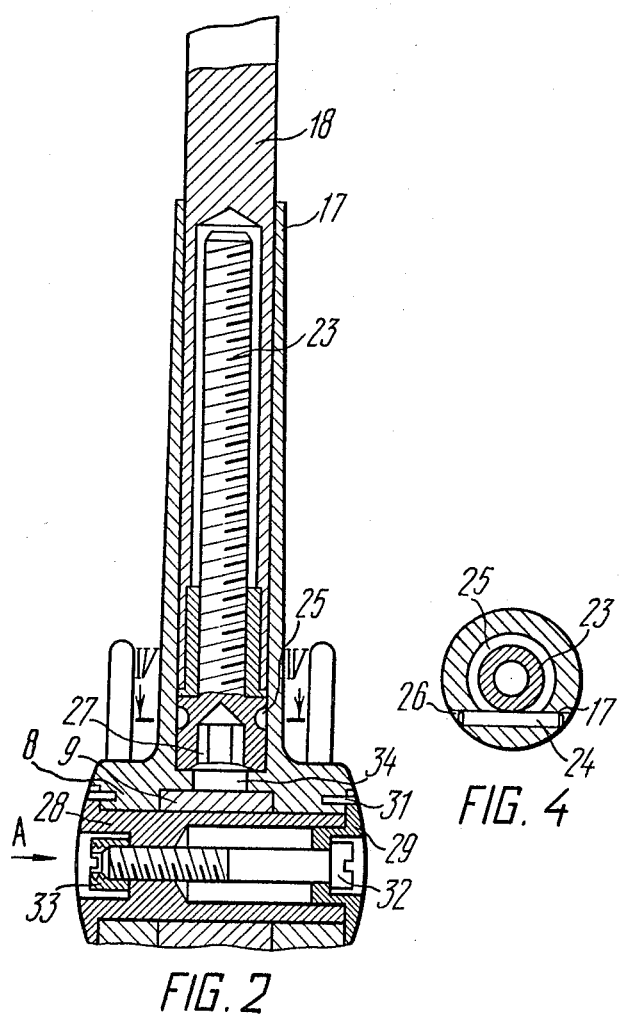
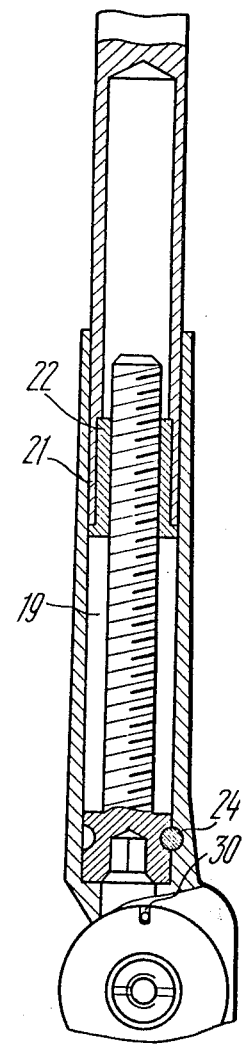

DEVICE FOR FUNCTIONAL RESTORATION OF AN EXTREMITY

FIELD OF THE INVENTION

The present invention relates generally to medicine and more specifically to devices for functional restoration of an extremity.

The invention can find most successful application in traumatology and orthopedics for a simultaneous provision of endoprostheses of the hip joint, knee joint and femoral diaphysis. The device can be used when simultaneously applying endoprostheses of the hip and knee joints following complete resection of the femoral bone, in various oncologic affections involving partial resection of the femoral diaphysis or retaining the latter, as is the case with the Strümpell-Marie-Bechterew disease (arthrosis deformans).

In addition, the invention is applicable in similar operations on the upper extremities.

BACKGROUND OF THE INVENTION

Known in the present state of the orthopedic art are some artificial knee joints (cf. USSR Inventor's Certificate No. 532,377, class A61F 1/04 of 1972; a catalogue of the firm "Howmedica" issued in Great Britain in 1973, indexes Nos. 2660-9, 2661-0, 2661-9). These artificial knee joints comprise two semijoints interlinked through a cylindrical articulation, and wedgelike antirotation spikes and rods made fast in the femoral and tibial bones.

One more artificial hip joint designed by K. M. Sivash is known to comprise an artificial cotyloid cavity and artificial femoral head and neck made as an integral piece, as well as a tapered fenestrated rod fixed in the medullary canal of the femoral diaphysis.

The devices discussed above are adapted for alloplasty of the knee joint or the hip joint alone and cannot be used for simultaneous prosthetic restoration of both the hip and knee joints with the femoral diaphysis either left in place or ablated. Thus, in the case where the femoral diaphysis is left in place, the tapered rods of the artificial knee and hip joints cannot be fixed in the medullar canal of the femoral bone since the same define a strictly definite length, while in the case where the femoral diaphysis is resected said tapered rods fail to provide locomotor function of the extremity since the same are not interlinked.

Still another device for the functional restoration of an extremity (cf. a catalogue of the firm "Howmedica" issued in Great Britain in 1973, index No. 2934-9, p. M3) is known to comprise an artificial hip joint associated with an artificial knee joint through an artificial femoral diaphysis. The artificial femoral diaphysis is made as a rod one of whose ends is inseparably linked to the artificial hip joint and the other end is inseparably linked to the artificial knee joint. Such a constructional arrangement of the device renders it inapplicable in operations, where the femoral diaphysis must and can in fact be retained. Application of the known device in question involves a greater degree of tissue traumatization as in this case the necessity arises of a complete resection of the femoral bone. The device cannot also be applied to patients whose femoral bones differ in length.

SUMMARY OF THE INVENTION

It is an essential object of the present invention to provide a device for functional restoration of an extremity that would reduce the degree of traumatization of the tissues involved and permits the retention of the femoral diaphysis if required.

It is another object of the present invention to provide a device for functional restoration of an extremity, which would make possible application of endoprostheses to patients whose femoral bones differ in length.

Said and other objects of the present invention are accomplished in a device for functional restoration of an extremity, incorporating: an artificial hip joint; an artificial knee joint; an artificial femoral diaphysis interconnecting said artificial hip joint with said artificial knee joint; said femoral diaphysis comprising: a cylindrical column inseparably linked to said knee joint and having a longitudinal geometric axis; a through cylindrical bore provided in said column lengthwise of its geometric axis; a double-ended rod; one of the ends of said rod inseparably linking said rod with said artificial hip joint; the other of the ends of said rod fitted in the bore of said column; a threaded sleeve fixed in position at the other end of said rod; a motion screw engageable with said threaded sleeve and rotatably mounted in said column for said rod to travel axially with respect to said column upon rotation of said motion screw.

The essence of the present invention resides in that in a device for functional restoration of an extremity, incorporating an artificial hip joint, an artificial knee joint and an artificial femoral diaphysis, which interlinks said artificial hip joint and knee joint, wherein the artificial femoral diaphysis is made up of a cylindrical column telescopically associated with a rod, said column having a through longitudinal bore and being inseparably linked to the artificial knee joint, while said rod is inseparably linked to the artificial hip joint with one of its end and is fitted in the column bore with its other end which carries a threaded sleeve fixed in position thereon and being engageable with a motion screw, said motion screw being rotatably mounted in the column for the rod to travel axially with respect thereto upon rotation of said motion screw.

Such a constructional arrangement of the device is instrumental in reducing the degree of traumatization of the tissues involved, in retaining the femoral diaphysis and in applying the device in patients whose femoral bone has any particular length due to the fact that in operations for, e.g., arthrosis deformans the rod inseparably linked to the artificial hip joint and carrying the threaded sleeve fixed rigidly thereon passes through the natural retained femoral diaphysis at the proximal end thereof, whereupon the cylindrical column inseparably linked to the artificial knee joint and carrying the motion screw is passed through said natural femoral diaphysis at the distal end thereof towards said rod, whereupon the device is integrated into a single whole.

Thus, the degree of traumatization of the tissues involved in the operation is reduced and the patient's femoral diaphysis is retained together with the muscular corset attached thereto.

It is expedient that the motion screw be mounted in the column by way of a lockpin passing through an annular groove made in the screw and through a corresponding hole provided in the column.

Rotation of the motion screw in the threaded sleeve permits adjustment of the artificial femoral diaphysis as for length, thereby enabling the device to be applied in patients having a femoral bone of any length.

The motion screw may have a socket to receive a key for lengthwise adjustment of the artificial femoral diaphysis to adjust in length.

BRIEF DESCRIPTION OF THE DRAWINGS

FIG. 2 is a section taken along the line II—II in FIG. 1, turned purposely through 90°;

FIG. 3 is a view facing the arrow A in FIG. 2; and

FIG. 4 is a section taken along the line IV—IV in FIG. 2.

DESCRIPTION OF THE PREFERRED EMBODIMENT

Figure 1:
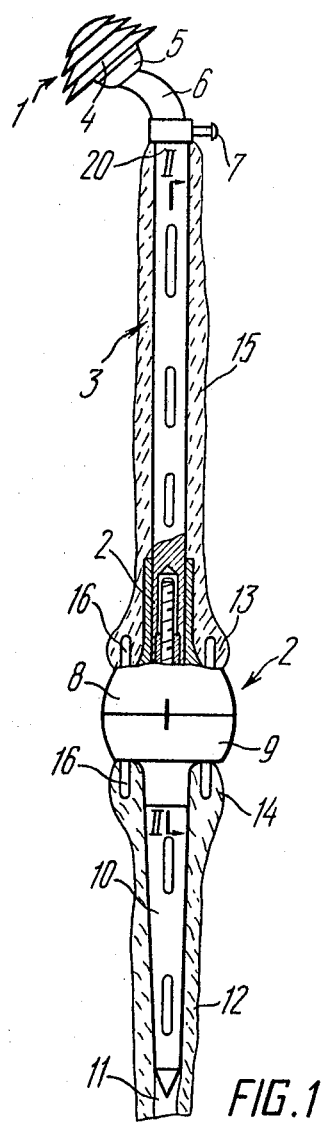
FIG. 1 is a general schematic view, partly in longitudinal section, of a device for functional restoration of an extremity, incorporating an artificial hip joint, knee joint and femoral diaphysis, according to the present invention.

The disclosed device for functional restoration of an extremity as illustrated in FIG. 1, comprises an artificial hip joint 1 and an artificial knee joint 2 interlinked through an artificial femoral diaphysis 3.

The artificial hip joint 1 has an endoprosthesis 4 of the cotyloid cavity, an artificial femoral head 5, an artificial femoral neck 6 and a nail 7 to hold the preliminarily resected greater trochanter to the hip joint 1. The artificial knee joint 2 is made up of two semijoints 8 and 9 of which the semijoint 9 is inseparably linked to a tapered rod 10 accommodated in a medullary canal 11 of a tibial bone 12, while the other semijoint 8 is associated with the artificial femoral diaphysis 3.

In order to hold the artificial knee joint 2 in respective condyles 13 and 14 of a femoral bone 15 and the tibial bone 12, provision is made for antirotation spikes 16 secured in position in the semijoints 8 and 9 of the artificial knee joint 2.

The artificial femoral diaphysis 3 illustrated in FIG. 2 is made up, according to the present invention, of a cylindrical column 17 and a rod 18 interlinked telescopically therewith. The cylindrical column 17 is inseparably linked to the artificial knee joint and has a through longitudinal bore 19 (FIG. 3).

The rod 18 is inseparably linked, through its end 20 (FIG. 1), to the neck 6 of the artificial hip joint, and is fitted in the bore 19 of the column 17 with its other end 21 (FIG. 3). The end 21 of the rod 18 carries a threaded sleeve 22 fixed in position thereon and engageable with a motion screw 23, which is rotatably mounted in the column 17 of the artificial knee joint for the rod 18 of the artificial femoral diaphysis 3 to travel with respect to the column 17 so as to adjust the length of the artificial femoral diaphysis 3.

The motion screw 23 is installed in the column 17 through a lockpin 24 (FIG. 4) passing through an annular groove 25 made in the motion screw 23 (FIG. 2) and through a hole 26 (FIG. 4) provided in the column 17 and corresponding to the groove 25.

In addition, the motion screw 23 mounted in the column 17 has a socket 27 (FIG. 2) to receive a key (not shown) for adjusting the length of the artificial femoral diaphysis 3.

The semijoints 8 and 9 of the artificial knee joint 2 are interlinked through a bush 28 (FIG. 2) provided on one side of the artificial knee joint 2, and a washer 29 located on the other side of the joint 2. Both the bush 28 and the washer 29 have slots 30 (FIG. 3) to accommodate pins 31, which ensure against spontaneous disassembling of the artificial knee joint 2. The pins 31 are locked in place in the semijoint 8 of the artificial knee joint 2. The bush 28 and the washer 29 are braced together with a screw 32 and a nut 33. The semijoint 8 of the artificial knee joint 2 has a hole 34 for the key to pass through and fit in the socket 27 of the motion screw 23. The semijoints 8 and 9, as well as the bush 28 and washer 29 are made of cobalt alloys, while all the rest of the components of the device for functional restoration of an extremity are made of titanium alloys.

The operation of implanting the device for functional restoration of an extremity is carried out as follows.

The femoral bone 15 (FIG. 1) is resected at the lesser trochanter, whereupon the entire trochanteric portion, the femoral head and neck is ablated. Then the knee joint is resected at the most prominent portion of the condyles 13 and 14 of the respective femoral bone 15 and tibial bone 12. Next the medullary canals of the femoral bone 15 and of the proximal portion of the tibial bone 12 are treated with special drills and reamers.

The device for functional restoration of an extremity must be disassembled prior to being implanted during the operation into the following components: the rod 18 inseparably linked to the artificial hip joint 1 and the cylindrical column 17 inseparably linked to the artificial knee joint 2 (FIG. 1) and accommodating the motion screw 23.

The artificial knee joint 2 must also be disassembled into the following pieces prior to the operation: the screw 32, the nut 33, the washer 29 and the bush 28.

The rod 18 is inserted into the preliminarily prepared (treated) medullary canal of the femoral bone 15, said rod being inseparably linked to the artificial hip joint 1 through its end 20 and having the threaded sleeve 22 at its other end 21.

To preclude the piston effect when passing the rod 18 through the medullary canal of the femoral bone 15, a taper endpiece (not shown) is screwed into the threaded sleeve 22. Once the rod 18 has been finally set in position within the medullary canal of the femoral bone 15, said tapered endpiece is dismantled and withdrawn at the resected knee joint end.

Then the semijoint 8 with the cylindrical column 17 accommodating the motion screw 23 is introduced into the femoral bone 15 at the resected knee joint end. The bottom end 21 of the rod 18 is inserted into the longitudinal bore 19 (FIG. 3) of the cylindrical column 17 (FIG. 2), while the motion screw 23 is engaged with the threaded sleeve 22.

Next a socket key is fitted into the socket 27 of the motion screw 23 through the hole 34 in the semijoint, in order to set precisely the required length of the artificial femoral diaphysis 3.

At the same time the antirotation spikes 16 are embedded into the condyles 13 of the femoral bone 15.

Thereupon the tapered rod 10 of the semijoint 9 of the artificial knee joint 2 is introduced into the medullary canal 11 of the tibial bone 12, while the antirotation spikes 16 are being embedded into the condyles 14 of the tibial bone 12.

Further on the semijoints 8 and 9 of the artificial knee joint 2 are united. To this end the bush 28 is set on one side and the washer 29, on the other side of the artificial knee joint 2 in such a manner that the pins 31 of the knee joint 2 should enter the slots 30 in said bush and said washer to ensure against spontaneous disassembling of the knee joint. Next the screw 32 is passed through the hole of the washer 29 and turned into threaded bush 28, and the nut 33 is turned onto the screw 32 using a special screwdriver.

Then the preliminarily resected trochanter is held to the artificial hip joint 1 by means of the nail 7. The wounds in the region of the hip and knee joints 1 and 2 are sutured layer-by-layer having established the drain tubes wherever necessary.

Practical application of the device for functional restoration of an extremity makes it possible to regain the locomotor functions of the affected extremity in patients suffering from severe lesions or diseases of the knee or hip joints, or of the femoral diaphysis.

Surgical treatment of such gravest diseases as Strümpell-Marie-Bechterew's, arthrosis deformans, coxarthroses accompanying various oncological affections, aided by the proposed device makes it possible to completely restore the lost functions of the affected extremity.

The proposed device may also be applied successfully for surgical treatment of osteopathies of the upper extremities, with the corresponding size corrections introduced.

What is claimed is:

1. A device for functional restoration of an extremity, comprising: an artificial hip joint; an artificial knee joint; and an artificial femoral diaphysis for interconnecting said artificial hip joint and said artificial knee joint; said femoral diaphysis including a cylindrical column inseparably linked to said knee joint and having a longitudinal geometric axis, a through cylindrical bore provided in said column along the geometric axis thereof, a double-ended rod, one of said ends of said rod inseparably linking said rod to said hip joint, the other of said ends of said rod fitted in said bore of said column, a threaded sleeve fixed in position at the other end of said rod, a motion screw engageable with said threaded sleeve and rotatably mounted in said column for axially moving said rod with respect to said column upon rotation of said screw, whereby the length of said artificial femoral diaphysis can be adjusted.

2. A device as claimed in claim 1, wherein said motion screw is fitted in said column with the aid of a lockpin which passes through an annular groove formed in said screw and through a hole formed in said column and aligned with said groove.

3. A device as claimed in claim 1, wherein said motion screw has a socket to receive a key for the lengthwise adjustment of said artificial femoral diaphysis.

* * * * *